United States Patent [19]

Szakasits et al.

[11] Patent Number: 5,049,509

[45] Date of Patent: * Sep. 17, 1991

[54] CHROMATOGRAPHIC ANALYZER

[75] Inventors: Julius J. Szakasits; Robert E. Robinson, both of Houston, Tex.

[73] Assignee: Shell Oil Company, Houston, Tex.

[*] Notice: The portion of the term of this patent subsequent to Aug. 13, 2002 has been disclaimed.

[21] Appl. No.: 121,425

[22] Filed: Nov. 16, 1987

Related U.S. Application Data

[63] Continuation-in-part of Ser. No. 750,343, Jun. 28, 1985, abandoned.

[51] Int. Cl.⁵ ............................................ G01N 33/00
[52] U.S. Cl. .................................... 436/140; 436/141; 436/142; 422/89; 422/93; 73/23.38; 55/386
[58] Field of Search ................. 436/55, 161, 139, 140, 436/141, 142; 422/70, 89; 73/23.38, 23.4; 55/386, 67, 197

[56] References Cited

U.S. PATENT DOCUMENTS

| | | | |
|---|---|---|---|
| 3,654,145 | 4/1972 | Brunnock et al. | 208/310 |
| 4,204,952 | 5/1980 | Snyder | 210/31 C |
| 4,384,471 | 5/1983 | Wentzel | 73/23.1 |
| 4,446,105 | 5/1984 | Dinsmore et al. | 422/70 |
| 4,534,207 | 8/1985 | Szakasits et al. | 73/23.1 |

Primary Examiner—David L. Lacey
Assistant Examiner—David Redding

[57] ABSTRACT

Methods and apparatus for analyzing a hydrocarbon sample are provided. The apparatus employs a highly polar column to separate the aromatics from non-aromatic components. The non-aromatic effluent from the highly polar column is passed to a 13X MSCOT column and a first less polar column. In a second configuration the highly polar column is backflushed into a second less polar column. The 13X MSCOT column separates isoparaffins, normal paraffins, and naphthenes by carbon number while the first less polar column individually separates the paraffins and naphthenes. The second less polar column is employed to separate individual aromatics.

The method for analyzing a hydrocarbon sample separates the aromatics of the sample from the isoparaffins, normal paraffins, and naphthenes. The isoparaffins, normal paraffins, and naphthenes are then separated and detected by carbon number. Simultaneously, the individual non-aromatic components are separated and detected. The aromatics that have been previously separated are then individually separated and detected.

10 Claims, 7 Drawing Sheets

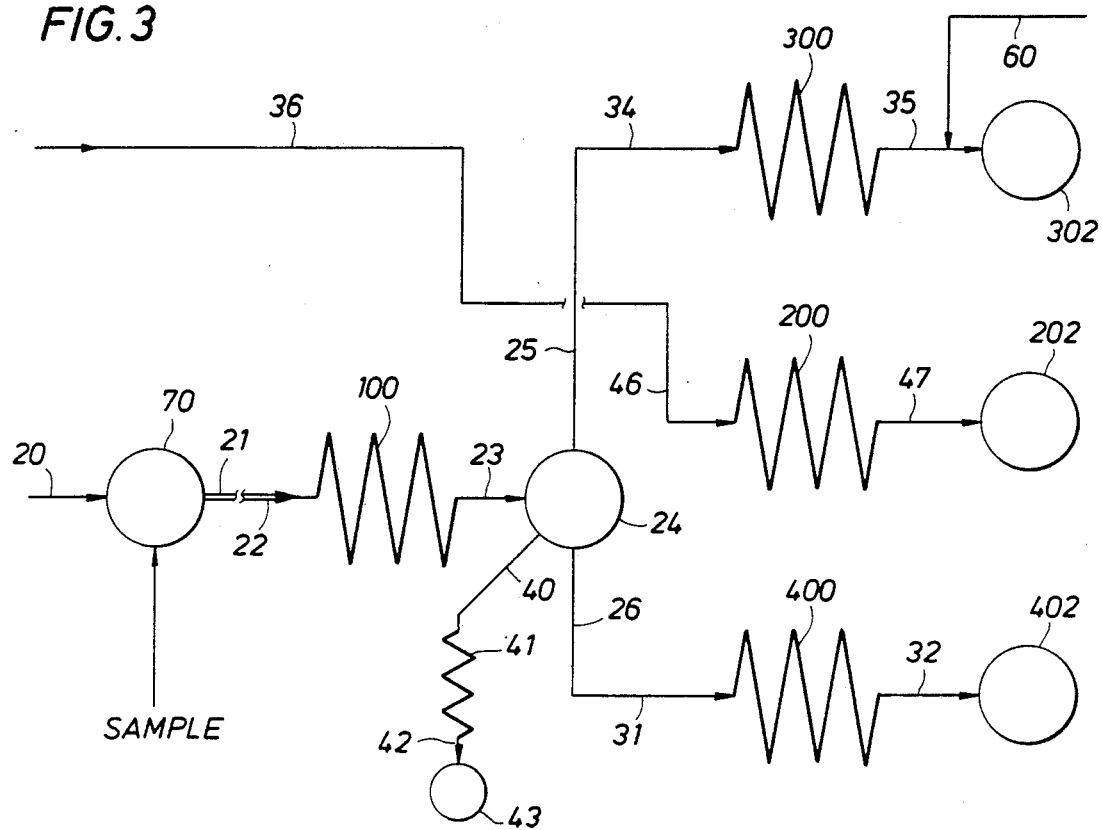
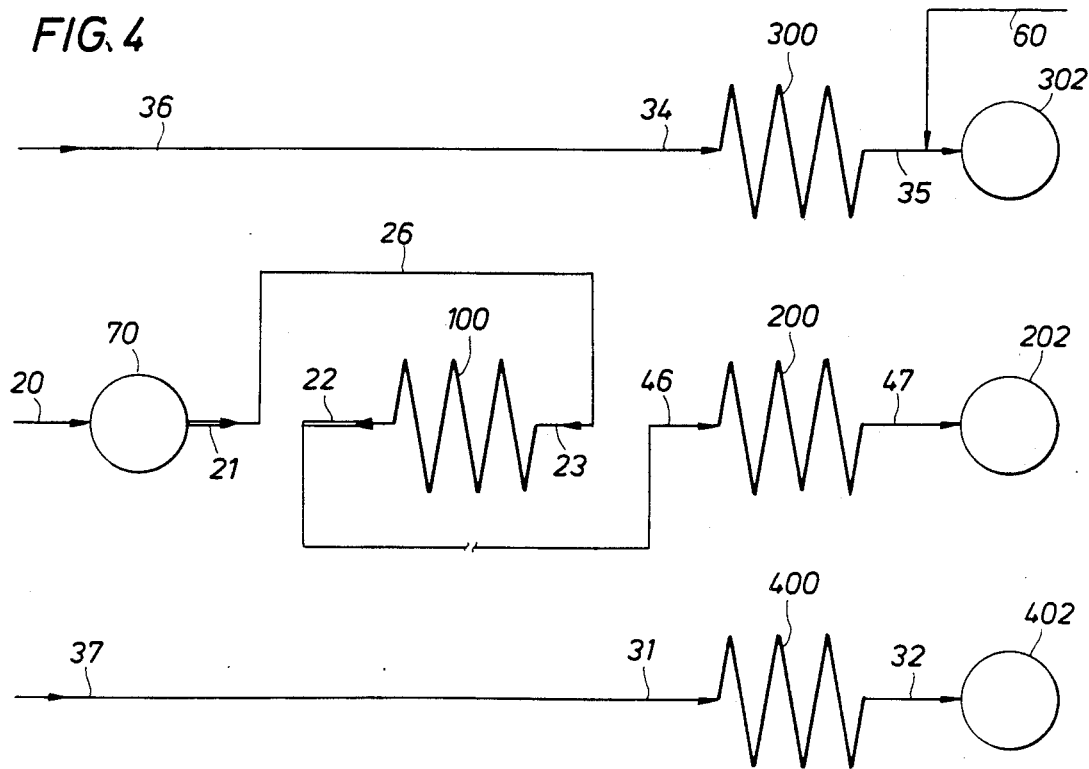

CHROMATOGRAPHIC ANALYZER

CROSS REFERENCE TO RELATED APPLICATION

This application is a continuation-in-part of U.S. application Ser. No. 750,343, filed June 28, 1985, and now abandoned.

BACKGROUND OF THE INVENTION

This invention relates generally to analysis of samples by gas chromatography, and more particularly relates to the analysis of hydrocarbon samples by gas chromatography. Relevant patents include U.S. Pat. Nos. 3,201,922 (Villalobos, issued Aug. 24, 1965), 3,654,145 (Brunnock et al, issued Apr. 4, 1972), 4,204,952 (Snyder, issued May 27, 1980), 4,234,315 (Scott, issued Nov. 18, 1980), 4,384,471 (Wentzel, issued May 24, 1983), 4,446,105 (Dinsmore et al, issued May 1, 1984), 4,534,207 (Szakasits et al, issued Aug. 13, 1985) and 4,577,492 (Holba et al, issued Mar. 25, 1986).

It is important to be able to analyze a hydrocarbon sample quickly and cheaply. This importance is particularly acute in the petrochemical and chemical industries. This is because there may be frequent changes in the composition of feedstocks employed in the various processes that are involved in either the petrochemical or chemical industries. This has created the need for an on-site instrument which can quickly provide an analysis of the feed and/or product composition during plant operation to ensure that the feed and product composition are within desired ranges. The failure at an early stage to recognize poor plant performance, which may result in out-of-specification products, can lead to a serious loss in economic revenues.

Prior art analysis has generally consisted of a combination of gas chromatography and analytical chemistry methods conducted in some central laboratory which is normally remote from the chemical or petrochemical plant. The employment of these two (gas chromatography and analytical chemistry) methods is usually a time consuming and expensive proposition. Further, it often results in a lengthy time period between the time when the sample is actually taken and when the results are made available to the plant. This may exacerbate any potential economic loss due to poor plant performance during this time.

These and other limitations and disadvantages of the prior art are overcome by the present invention, however, and improved gas chromatographic methods and apparatus are provided for analyzing hydrocarbon samples.

SUMMARY OF THE INVENTION

In a preferred embodiment of the present invention, apparatus and method are provided for analyzing hydrocarbon samples. The preferred method for analyzing a hydrocarbon sample analyzes the sample for isoparaffins, normal paraffins, naphthenes, and aromatics. This preferred method separates the aromatics of the sample from the isoparaffins, normal paraffins and naphthenes, and thereafter the individual aromatics are separated and detected. The fraction containing separated isoparaffins, normal paraffins and naphthenes is further separated and detected as isoparaffins, normal paraffins and naphthenes by carbon number.

The presently preferred apparatus for analyzing a hydrocarbon sample consists of four gas chromatography columns. A suitable sample injector injects a sample into the first column. The first column is a highly polar column which is employed to separate the aromatics fraction from the non-aromatics fraction. This highly polar column is selectively interconnectable with a second column, which is a 13X molecular sieve column, and a third column, which is a first less polar column than the highly polar column, or with a fourth column. The highly polar column is interconnectable with the fourth column so that the highly polar column may be backflushed into the fourth column, which is a second less polar column than the highly polar column. The 13X molecular sieve coated capillary column separates isoparaffins, normal paraffins and naphthenes by carbon number. The first less polar column separates the individual paraffins and naphthenes. The second less polar column separates the individual aromatics.

The presently preferred apparatus also includes appropriate valve means, detection means, means for controlling the temperature of each column and means for supplying appropriate carrier gases at appropriate flow rates to the various columns. The invention uses a plurality of columns and detectors to expand the analyzer scope and to shorten the analysis time by performing various analyses concurrently.

The present invention provides detailed analysis in approximately one and one-half hours of the isoparaffins, normal paraffins, naphthenes and aromatics of a hydrocarbon sample boiling below about 255° C., including the $C_5/C_6$ ring naphthenes distribution within that sample. The data provided by the present invention can be used as, for example but not limited to, an input into a plant model to determine what control actions are necessary to optimize a reformer process.

It is an object of the present invention to provide methods and apparatus for analyzing a hydrocarbon sample.

Accordingly, these and other objects and advantages of the present invention will become apparent from the following detailed description wherein reference is made to the figures in the accompanying drawings.

BRIEF DESCRIPTION OF THE DRAWINGS

FIG. 3 is a simplified flow diagram of the analyzer of FIG. 1 in one operating configuration.

FIG. 4 is a simplified flow diagram of the apparatus of FIG. 1 in a second operating configuration.

DESCRIPTION OF PREFERRED EMBODIMENTS

Figure 1:
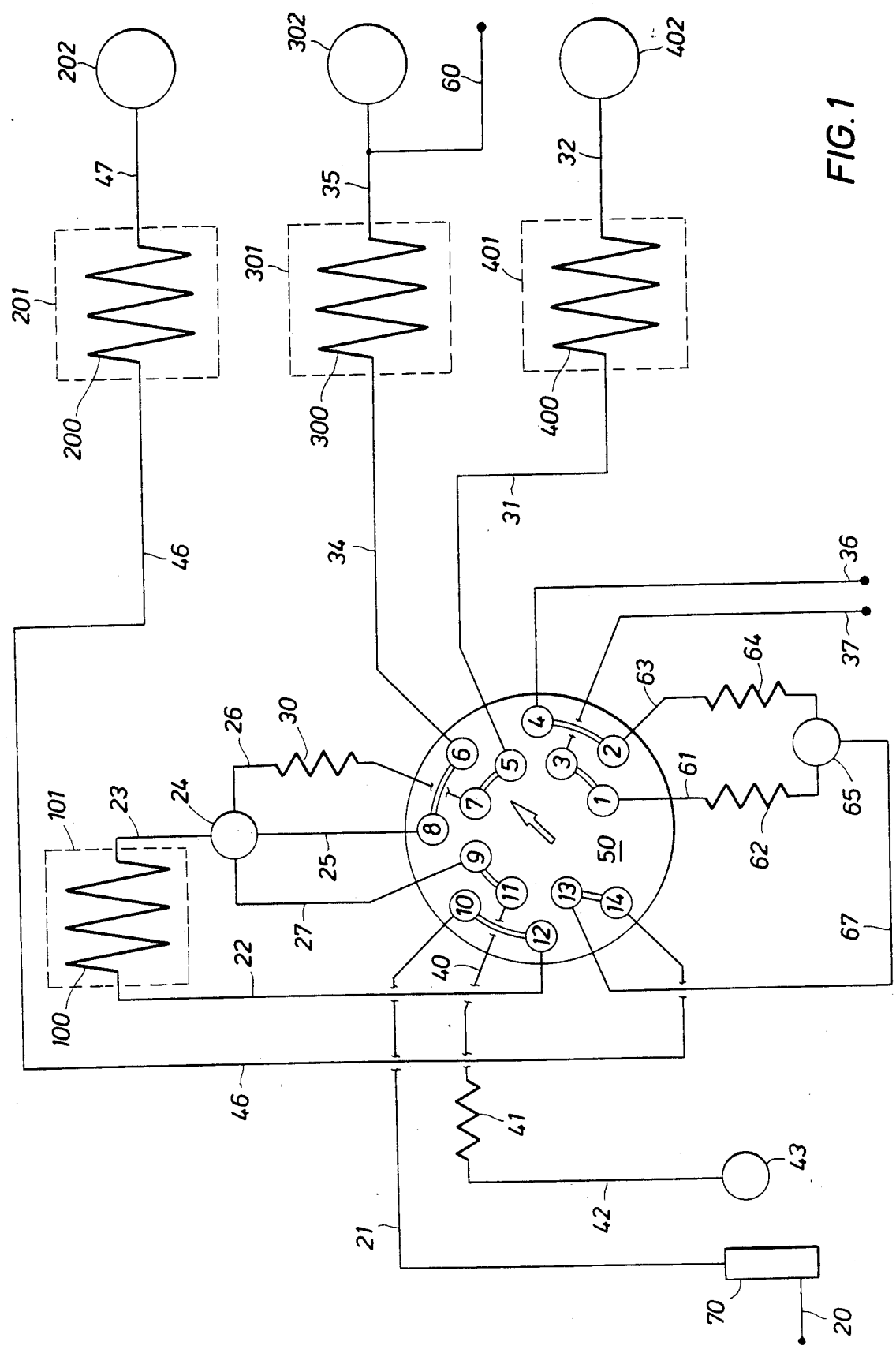
FIG. 1 is a diagrammatic view of one embodiment of a chromatographic analyzer according to the present invention.

Referring now to FIG. 1 there may be seen a simplified diagrammatic view of one embodiment of a chromatographic analyzer of the present invention. More particularly, there may be seen four columns, i.e., column 100, column 200, column 300 and column 400. There may also be seen a 14-port valve 50, sample injector 70 and carrier gas supply lines 20, 36 and 37. It should be noted that valve 50 has two operating positions and is depicted in its first operating position in FIG. 1 and in its second operating position in FIG. 2.

Continuing to refer to FIG. 1, a suitable carrier gas, which is preferably ultra pure hydrogen, is injected into line 20 which sweeps a hydrocarbon sample, which has been injected in sample injector 70 by appropriate means, from the sample injector 70 through line 21 into valve 50. Line 21 is connected to port 10 of valve 50. Valve port 10 is internally connected to valve port 12 when valve 50 is in its first operating position. Valve port 12 is, in turn, connected to line 22 which is, in turn, connected to column 100, which is preferably a highly polar column.

Column 100 may be any suitable metal tubing and may have a length of from about 1 to about 5 meters and an inside diameter of from about 1.5 to about 3.0 millimeters. Preferably, column 100 is a stainless steel tube having a length of about 4 meters and an inside diameter of about 2.3 millimeters, with BC 150 stationary phase, which is available from Supelco Inc. of Bellefonte, Penn., on Chromosorb-P AW, DMCS, to make the non-aromatics from aromatics separation. The mesh size is preferably about 100/120 mesh. Alternatively, BC 120 stationary phase, available from Supelco Inc. may also be employed.

Column 100 may be contained in a suitable temperature programmable oven 101 for maintaining the temperature of column 100 at a constant temperature, as determined by a suitable controller or computer 600. The outlet from column 100 is line 23 which is interconnected with splitter 24. The effluent from highly polar column 100 in line 23 is split into three portions by splitter 24. A portion of the effluent travels down each of three lines 25, 26, 27. Line 26 includes a flow restricter 30. Continuing to refer to FIG. 1, isothermal, high temperature splitter 24 is connected to port 9 of valve 50 and interconnected to port 11 in valve 50 in its first position. High flow is maintained in line 27 to reduce sample loading on the capillary columns 300 and 400. Splitter 24 venting is regulated by restrictor 41 connecting it to valve 50. Excess, vented hydrogen exits through line 42 and is combusted in a burner 43 similar in construction to an FID (flame ionization detector). The burner (not shown) for the high flow splitter system 24 (including arms 25, 26, 27, restrictor 30, and the high flow vent line 42) may be equipped with a temperature (flame on) sensor and an automatic igniter.

Line 25 is connected to port 8 of valve 50. Port 8 of valve 50 is connected internally to port 6 of valve 50 when valve 50 is in its first operating position. Port 6, in turn, is connected to line 34 which is interconnected with column 300. Column 300 is preferably a 13X molecular sieve coated open tubular (MSCOT) column. The details of preparing such a column are discussed in copending and commonly assigned application Ser. No. 602,626 filed Apr. 23, 1984, now abandoned, and refiled as patent application Ser. No. 052,170 filed May 19, 1987.

The finely divided particle layer provides a high resolution separation of naphthenes, normal paraffins and isoparaffins boiling up to about 255° C. by carbon number. Column 300 may be from about 50 meters to about 150 meters in length and may have an inner diameter of from about 0.1 millimeters to about 0.5 millimeters. Preferably, column 300 is about 100 meters of a fused silica capillary tube with an inner diameter of about 0.5 millimeters, for general analysis use. Fused silica is preferred because of its ability to operate at lower temperatures and because it is inert. While metal tubing may be employed, some metals may cause "cracking" of the sample, and create a large "tail" from impurities which are sometimes found in metal tubing. For analysis of feedstocks that also are analyzed by column 400 (as noted later herein) column 300 has a preferred length of about 50 meters. However, for analysis of products that do not contain high concentrations of naphthenes and if a $C_5/C_6$ ring naphthene separation is not important column 400 may be eliminated and column 300 then has a preferred length of about 100 meters to achieve essentially the same separations as column 400 would achieve. If a $C_5/C_6$ ring naphthene separation is important, column 400 may still be eliminated if the naphthene content is less than about 5%.

Column 300 may also be in a suitable temperature programmable oven 301. The temperature of oven 301 may be programmed by, for example, a suitable computer or controller 600 to provide suitable heating of column 300 to facilitate analysis of a sample. The heating program employed for oven 301 depends upon the type and length of column 300. For example, for an approximately 100 meter fused silica column having an about 0.50 millimeter inner diameter, the multi-level temperature programming may be: starting at about 70° C., having an increasing ramp of about 10° C./min. up to about 150° C., then 5° C./min to about 240° C. and then a slower ramp of about 2° C./min. to about 320° C. to enhance separation. Other temperature programs may also be employed, as are well known in the art. The effluent from column 300 is connected by line 35 to a suitable detector 302. Preferably, detector 302 is a flame ionization detector. A sweep inert gas, preferably nitrogen, or argon, or carbon dioxide is provided in line 60 and mixed with the effluent in line 35, ahead of detector 302.

Line 26 is connected to port 7 of valve 50. However, line 26 preferably includes flow restricter 30 in its line. Port 7 is interconnected with port 5 of valve 50 when valve 50 is in its first operating position. Port 5 of valve 50 is connected to line 31 which is also interconnected with column 400.

Column 400 is preferably a less polar column than highly polar column 100. Column 400 may be from about 100 meters to about 125 meters in length and have an inner diameter of from about 0.25 millimeters to about 0.32 millimeters and contain a uniform film of a less polar phase than column 100 of thickness from about 0.75 microns to about 1.0 microns. Examples of such less polar phases that are stable are methyl and phenyl silicone in fixed ratios, methyl silicone by itself, vinyl-phenyl-methyl silicone, polyethylene-polypropylene glycol or cyanopropyl silicone. Column 400 may be made from any suitable metal, fused silica, or glass tubing. Preferably, column 400 is fused silica tubing having a length of about 100 meters and an inside diameter of about 0.25 millimeters, containing a uniform film of methyl silicone about 1.0 micron thick.

Column 400 may also be disposed in a suitable temperature programmable oven 401. The temperature of oven 401 may be programmed by a suitable controller or computer 600 to provide suitable heating to column 400 during its analysis. For example, for a 100 meter fused silica column having a 0.25 millimeter inner diameter containing a uniform 1.0 micron thick film of methyl silicone, the multi-level programming may be: starting at about 40° C., having a gradually increasing rate of increase from about 1° C./min to about 60° C. and then increasing the rate to about 5° C./min to about 90° C., and then about 10° C./min to about 300° C. Other temperature programs may be employed, as are well known in the art. The effluent from column 400 is connected to a suitable detector 402 by line 32. Preferably, detector 402 is a flame ionization detector.

Figure 2:
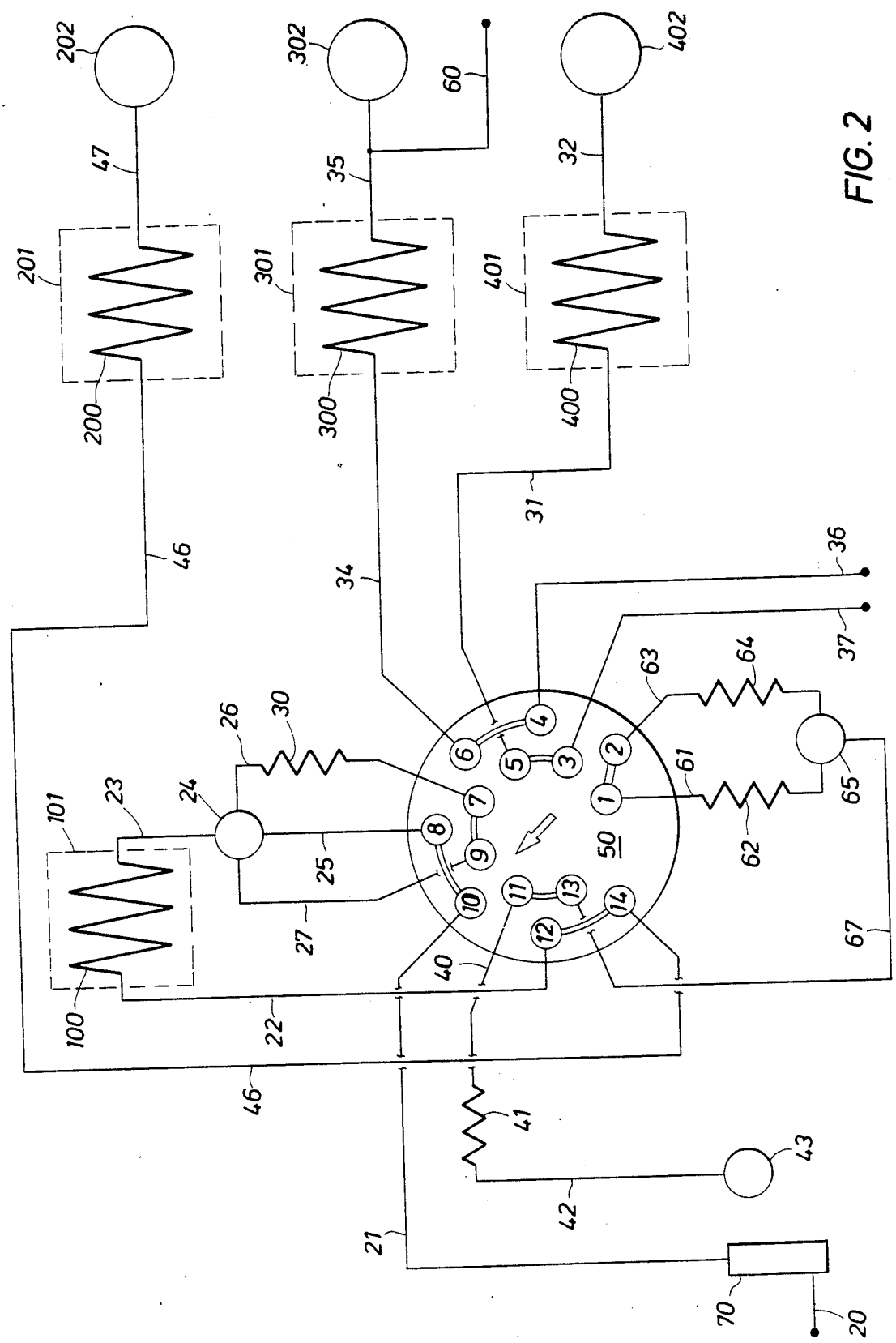
FIG. 2 is a diagrammatic view of a portion of the analyzer depicted in FIG. 1 in a different operating position.

FIG. 3 depicts, in a simplified flow diagram, the hereinbefore described flow paths of FIG. 1 when valve 50 is in its first operating position, but omits valve 50. FIG. 2 illustrates the second operating position of valve 50. FIG. 4 is a simplified flow diagram of the apparatus of FIG. 2 when valve 50 is in its second operating position, but omits valve 50. In this second position port 1 is interconnected with port 2, port 3 is connected with port 5, port 4 is connected with port 6, port 7 is interconnected with port 9, port 8 is interconnected with port 10, port 11 is interconnected to port 13 and port 12 is interconnected to port 14. This second operating position of valve 50 is employed to backflush the aromatics portion of a hydrocarbon sample from the column 100 into column 200. While this backflushing operation is occurring, separation is occurring on columns 300 and 400.

Referring now to FIG. 2 and to FIG. 4, it may be seen that an appropriate carrier gas, which is preferably hydrogen, is supplied to and flows down lines 36 and 37 to valve 50. Line 37 is connected to port 3 of valve 50, which, in the second operating position of valve 50, is interconnected with port 5 (see FIG. 2). Port 5, in turn, is connected with line 31 which is interconnected with column 400. Thus, line 37 supplies a carrier gas to column 400 to allow this column to continue its analysis of the portion of the hydrocarbon sample which has been injected upon it, while highly polar column 100 is being backflushed onto column 200, and also during the analysis of the aromatics backflushed onto column 200.

Continuing to refer to FIG. 2 and FIG. 4, line 36 is interconnected with port 4 of valve 50 which, in its second operating position, is interconnected with port 6 (see FIG. 2). Port 6 is, in turn, connected to line 34 which is interconnected with column 300. Thus, line 36 supplies an appropriate carrier gas, which is preferably ultra pure hydrogen, to column 300 during the backflushing of highly polar column 100 onto column 200 and also during the analysis of the aromatics backflushed onto column 200.

Referring to FIG. 1, it may be seen that an appropriate ultra pure carrier gas, preferably hydrogen, is supplied to and flows down through lines 36 and 37 to valve 50. Line 37 is connected to port 3 which is internally connected to valve port 1 when valve 50 is in its first position. Similarly, line 36 is connected to port 4, which is internally connected to port 2 when valve 50 is in its first position. Port 1 of valve 50 is connected with line 61 to carrier flow restrictor 62. Carrier flow restrictor 62 is calibrated to maintain the hydrogen carrier gas pressure in line 37 when valve 50 is in its first position to be equal to, or about 5 psig above, the operating inlet pressure of column 400 at the instant after valve 50 is switched to its second position. Similarly, port 2 with line 63 is connected to restrictor 64. Carrier flow restrictor 64 is calibrated to maintain the hydrogen carrier gas pressure in line 36, when valve 50 is in its first position, to be equal to, or about 5 psig above, the operating inlet pressure of column 300 at the instant after valve 50 is switched to its second position. Carrier gas flows from restrictors 62 and 64 are combined and directed through line 67 connecting to port 13 of valve 50, which is internally connected to port 14, which is connected to column 200 by line 46, to maintain carrier gas purge flow in column 200 when valve 50 is in its first position. Restrictors 62 and 64 thus assure complete sample transfer to columns 300 and 400.

Carrier gas 20 flowing through injector 70 and line 21 is interconnected with line 25 when valve 50 is in its second operating position (see FIG. 2). This allows carrier gas 20 to flow through line 25 into splitter 24, back down line 23, into polar column 100. The retarded materials on column 100 are then backflushed down line 22 to port 12 of valve 50. Port 12 of valve 50 is interconnected with port 14, when valve 50 is in its second operating position (see FIG. 2). These backflushed materials when valve 50 is in its second operating position, pass out of column 100 through line 22 connecting to port 12 of valve 50, down line 46 to column 200, as depicted in FIG. 4.

The alternate path for the effluent from column 100 is down line 46 which is interconnected with column 200. Column 200 is preferably a less polar column than highly polar column 100. However, column 200 may contain substantial amounts of polar material to enhance the separation of the aromatic components, but should be less polar than highly polar column 100. Examples of such less polar materials are phenyl and methyl silicone in various ratios or methyl silicone alone, or any other material noted hereinbefore for use in column 400. Column 200 may be from about 10 meters to about 50 meters in length and have an inner diameter of from about 0.30 millimeters to about 0.60 millimeters, and contain a uniform phase layer having a thickness of about 1 micron to about 8 microns. Column 200 may be made from any suitable metal, fused silica, or glass capillary tubing. Preferably, column 200 is a fused silica tubing having a length of about 30 meters and an inside diameter of about 0.54 millimeters, containing a uniform layer of methyl silicone or phenyl-methyl silicone about 3.0 microns thick.

Column 200 may also be contained in a temperature programmable oven 201. Oven 201 is preferably the same as oven 401, i.e. oven 401 may contain both column 200 and column 400. When column 200 is in oven 401, the length and coating thickness of column 200 as well as the flow rate of carrier gas through column 200 are optimized for the best separation of aromatics while undergoing the temperature program of oven 401. When column 200 is in its own separate oven 201, a suitable temperature program may be employed depending upon the length, coating thickness and flow rate of column 200. Suitable temperature programs are well known in the art. Column 200 is preferably interconnected with a suitable detector 202 by line 47. Preferably, detector 202 is a flame ionization detector.

The operation of the analyzer, including operation of the valves, the temperature programming of the ovens, and the recording of any output from the detectors may be under the control of a suitable computer/controller 600. This computer/controller may also include suitable data manipulation and output formating functions. The detectors (202, 302, 402) may alternatively include appropriate chart recorders and/or analog-to-digital converters for input into computer/controller 600.

The operation of the process analyzer of the present invention is described as follows. The sample is injected into the analyzer through sample injector 70 and carried by carrier gas 20 into column 100. Column 100 retards the aromatics of the sample and allows the remainder of the sample and carrier gas to pass out through line 23. The effluent from column 100 is then split with a portion of it venting to a burner similar in design to a flame ionization detector. The remaining portions are diverted to column 300 and column 400 through appropriate valving and line connections as discussed hereinabove. This is most easily seen in FIG. 3.

Before benzene would elute from column 100, valve 50 is switched from its first operating position to its second operating position (which is indicated in FIG. 2). Simultaneously with the switching of valve 50, carrier gas flow restrictors 62 and 64, connecting to ports 1 and 2 of valve 50 with lines 61 and 63, will prevent incomplete sample transfer to columns 300 and 400 from column 100 by eliminating the possibility of sample flowing back to the carrier gas lines after valve 50 is switched to its second position. Carrier gas from line 37 is now supplied to column 400 as noted hereinabove and oven 401 begins its temperature program. Carrier gas from line 36 is now supplied to column 300 as noted hereinabove and oven 301 begins its temperature program.

Column 300, which is preferably a 13X MSCOT column, separates the isoparaffins, normal paraffins, and naphthenes by carbon number. These isoparaffins, normal paraffins, and naphthenes are detected by detector 302 by carbon number. Column 400 which is preferably a fused silica less polar coated column is used to separate individually the paraffins, isoparaffins, and naphthenes, which are detected by a suitable detector 402. As noted hereinbefore, if there is less than about 5% naphthenes (when $C_5/C_6$ ring separation is important) then column 400 may be eliminated and column 300 lengthened somewhat to obtain better component separations.

Concurrent with the separation occurring on columns 300 and 400, column 100 is being backflushed into column 200. This is most clearly illustrated in FIG. 4. This backflushing of column 100 sweeps the aromatics that were retarded on column 100 into column 200.

Separation by carbon number of the normal paraffins, isoparaffins, and naphthenes occurs on the 13X MSCOT column. Column 400 includes a detailed component separation of the individual naphthenes through at least about $C_8$.

For those products or feedstocks that contain less than about 5% naphthenes (when $C_5/C_6$ ring splits are important), the separation of individual components from column 400 may be duplicative of the separation obtained on only column 300 if column 300 is lengthened slightly, as discussed hereinbefore. Thus, when less than about 5% naphthenes (when $C_5/C_6$ ring splits are important) is present, column 400 may be eliminated and column 300 increased in length to achieve essentially the same separation.

For those products or feedstocks that have a very high naphthene content (i.e., such that binaphthenes and higher naphthenes are present), any bi- and higher naphthenes will not elute before benzene and will thus be included in the held up aromatics portion in column 100. However, these bi- and higher naphthenes may be separated and detected separately from the aromatics by column 200 and its associated detector 202. Computer/controller 600 may then take the data for these bi- and higher naphthenes and insert it in the appropriate table or chart corresponding to the components identified by column 400 and/or column 300.

Thus, computer/controller 600 may know for all the columns employed what elution times (and corresponding peaks) correspond to what components by column and may make appropriate data adjustments, such as those described hereinbefore, for the final output data from the analyzer of the present invention. Final output is generated by summing the area concentrations representing the separated components on column 200 and detected with detector 202 and stored in its corresponding data file in computer 600, with the concentrations representing the separated components on column 300 and detected with detector 302 and stored in its corresponding file in computer 600. The summed components of the two files in the computer are normalized to 100%. Because the material separated on column 400 is equal to that separated on column 300, the contents on peak file generated by detector 402 connected to column 400 are normalized in computer 600: 100%—aromatics content of the sample. Additional calculations may also be made as appropriate to satisfy user requirements.

Figure 5:
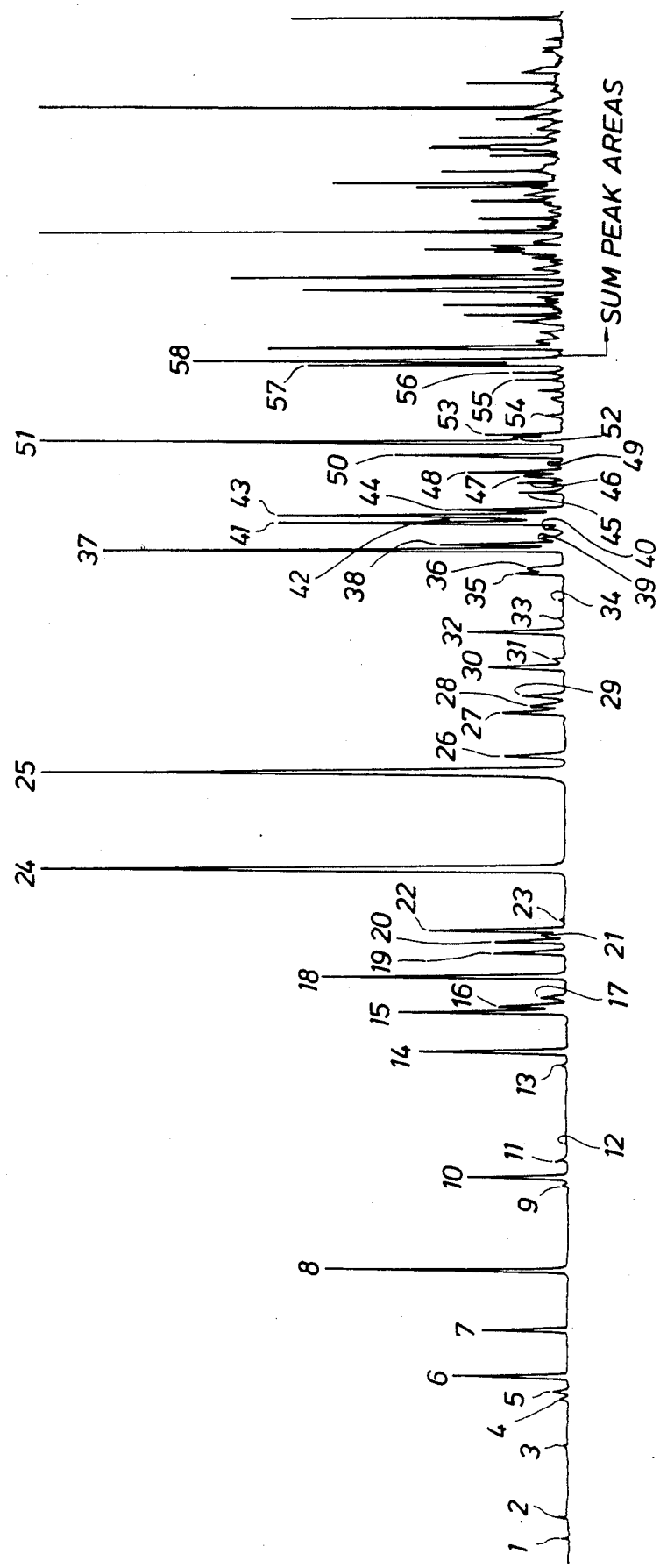
FIG. 5 is a typical chromatogram of the component-by-component separation of a non-aromatic fraction of a typical hydrocarbon sample with the first less polar column of the analyzer of FIG. 1.
Figure 6:
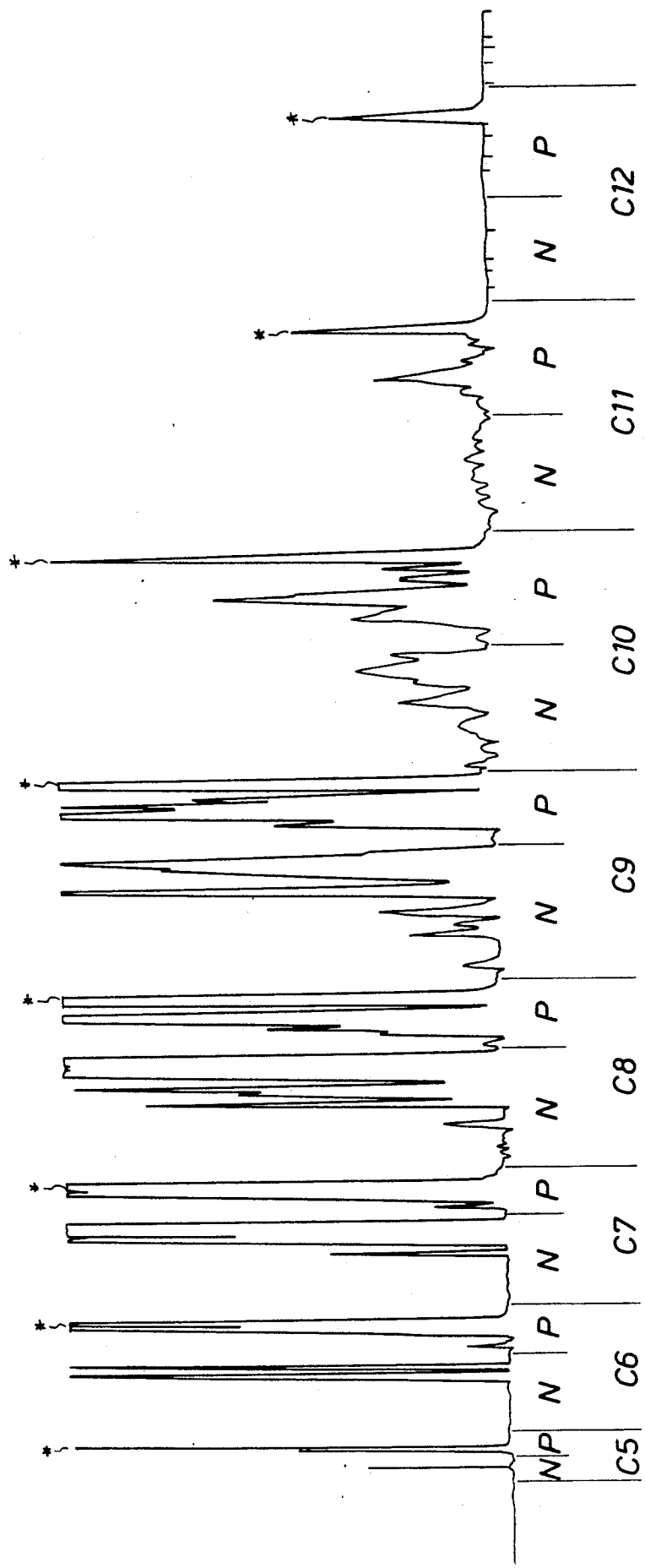
FIG. 6 is a chromatogram of the normal paraffins, naphthenes, and isoparaffins by carbon number separation of a typical hydrocarbon sample with the 13X MSCOT column of the analyzer of FIG. 1.
Figure 7:
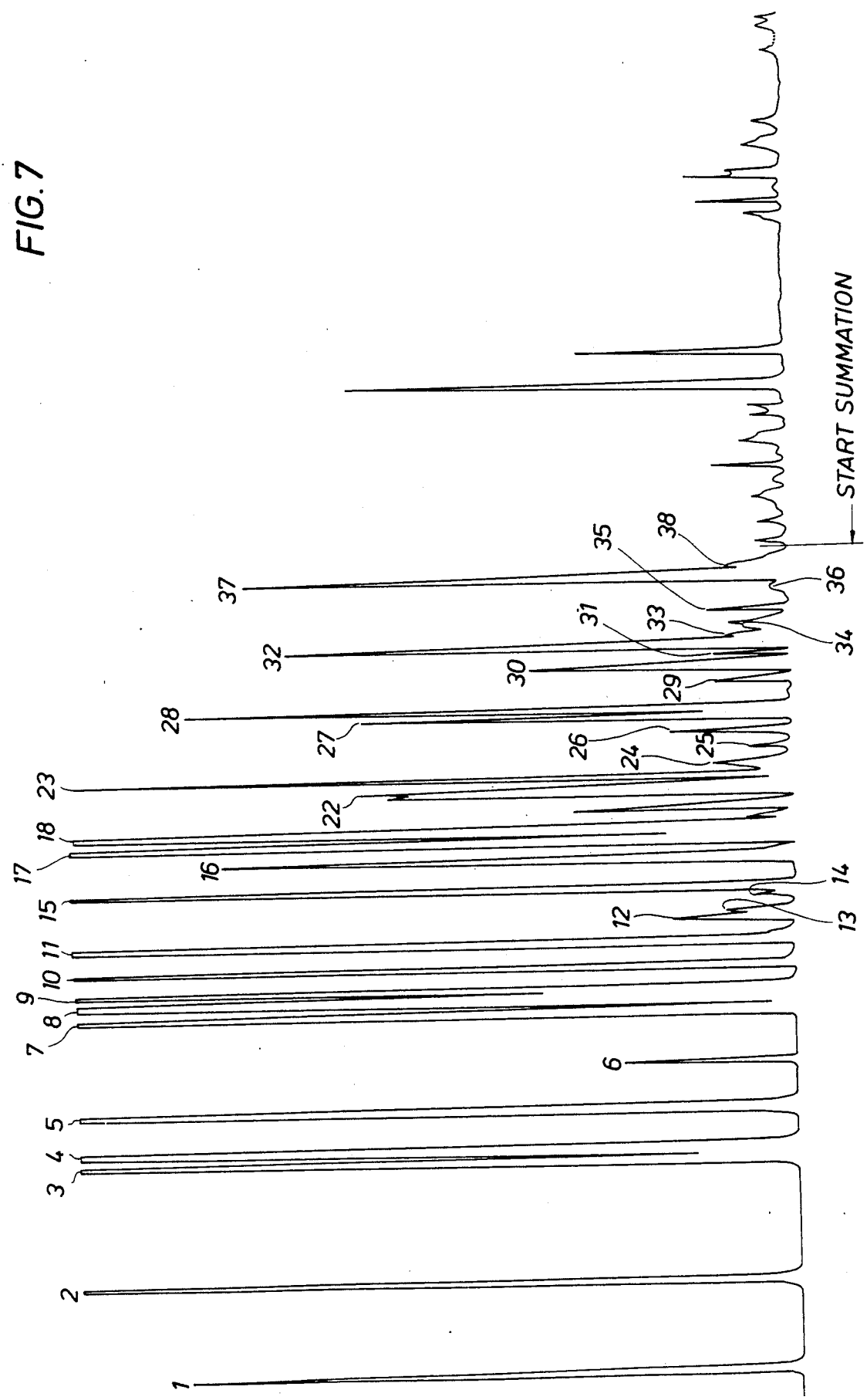
FIG. 7 is a chromatogram showing the separation of the aromatics from a typical hydrocarbon sample with the second less polar column of the analyzer of FIG. 1.

FIGS. 5-7 depict component separations that reasonably portray the actual data from the columns of the apparatus of the present invention.

FIG. 5 depicts the component separation of a representative hydrocarbon sample, from column 400 as detected by detector 402. Column 400 separates the sample by individual components from $C_1$ through at least $C_8$. The column used for this chromatogram was an approximately 100 meter fused silica tubing having an inside diameter of about 0.25 millimeters, containing a uniform coating of methyl silicone about 1.0 micron thick and subjected to the temperature program noted hereinbefore as an example for column 400. Routinely in the area of catalytic reforming, only $C_1$ through about $C_8$ are identified individually from a practical standpoint, as extensions beyond about $C_9$ are summed all together. The peaks identified in FIG. 5 are defined in Table 1.

FIG. 6 depicts the component separation of the representative sample of FIG. 5 obtained by column 300 as detected by detector 302. It illustrates the separation of the normal paraffins, isoparaffins, and naphthenes by carbon number through $C_{12}$. The column used for this chromatogram was an approximately 50 meter stainless steel tubing having an inside diameter of about 0.5 millimeters, and subjected to the temperature program noted hereinbefore as an example for column 300. The normal paraffin peak is denoted by an asterisk immediately above the peak for each carbon number between $C_5$ and $C_{12}$, as shown in the example (FIG. 6). However, separation of paraffins and naphthenes can be made through $C_{13}$.

FIG. 7 depicts the aromatic components separation of the sample of FIG. 5 obtained by column 200 as detected by detector 202. The column used to obtain this chromatogram was an approximately 30 meter fused silica tubing having an interior diameter of about 0.54 millimeters, containing about a 3 micron thick coating of 5% phenyl/95% methyl silicone, and subjected to the temperature program of column 400, noted hereinbefore as an example. The peaks identified in FIG. 7 are defined in Table 2. As illustrated in FIG. 7, additional peaks are detected but are not normally identified for practical reasons, as noted hereinbefore, but are summed all together to obtain a greater than about $C_{11}$ identification.

The column employed as column 100 to make the aromatics from non-aromatics separation for FIGS. 5-7 was an approximately 4 meter stainless steel tubing having an inside diameter of about 2.3 millimeters employing 100/120 mesh Chromosorb-P AW, DMCS, having BC 150 as a stationary phase, and held isothermally at a temperature of 145° C.

TABLE 1

Identification of Chromatogram (FIG. 5)

1. Isopentane
2. n-Pentane
3. 2,2-Dimethylbutane
4. Cyclopentane
5. 2,3-Dimethylbutane
6. 2-Methylpentane
7. 3-Methylpentane
8. n-Hexane
9. 2,2-Dimethylpentane
10. Methylcyclopentane
11. 2,4-Dimethylpentane
12. 3,3-Dimethylpentane
13. 2,2,3-Trimethylbutane
14. Cyclohexane
15. 2-Methylhexane
16. 2,3-Dimethylpentane
17. 1,1-Dimethylcyclopentane
18. 3-Methylhexane
19. 1-Cis-3-Dimethylcyclopentane
20. 1-Trans-3-Dimethylcyclopentane
21. 3-Ethylpentane
22. 1-Trans-2-Dimethylcyclopentane
23. 2,2,4-Trimethylpentane
24. n-Heptane
25. Methylcyclohexane+1-Cis-2-Dimethylcyclopentane+2,2-Dimethylhexane
26. 1,1,3-Trimethylcyclopentane
27. Ethylcyclopentane
28. 2,5-Dimethylhexane
29. 2,2,3-Trimethylpentane+2,4-Dimethylhexane
30. 1,Trans-2,Cis-4-Trimethylcyclopentane
31. 3,3-Dimethylhexane
32. 1,Trans-2,Cis-3-Trimethylcyclopentane
33. 2,3,4-Trimethylpentane
34. 2,3,3-Trimethylpentane
35. 2,3-Dimethylhexane
36. 2-Methyl-3-Ethylpentane+1,1,2-Trimethylcyclopentane
37. 2-Methylheptane
38. 4-Methylheptane
39. 3,4-Dimethylhexane+3-Methyl-3-Ethylpentane
40. 1,Cis-2,Trans-4-Trimethylcyclopentane
41. 3-Methylheptane
42. 3-Ethylhexane
43. 1-Cis-3-Dimethylcyclohexane+1,Cis-2,Trans-3-Trimethylcyclopentane
44. 1-Trans-4-Dimethylcyclohexane
45. 1,1-Dimethylcyclohexane
46. 1-Methyl-Trans-3-Ethylcyclopentane
47. 1-Methyl-Cis-3-Ethylcyclopentane
48. 1-Methyl-Trans-2-Ethylcyclopentane
49. 1-Methyl-1-Ethylcyclopentane
50. 1-Trans-2-Dimethylcyclohexane
51. n-Octane
52. 1,Cis-2,Cis-3-Trimethylcyclopentane
53. 1-Trans-3-Dimethylcyclohexane+1-Cis-4-Dimethylcyclohexane
54. Isopropylcyclopentane
55. 1-Methyl-Cis-2-Ethylcyclopentane+2,4-Dimethylheptane
56. 1-Cis-2-Dimethylcyclohexane
57. n-Propylcyclopentane
58. Ethylcyclohexane

TABLE 2

Aromatics Column Separation (FIG. 7)

1. Benzene
2. Toluene
3. Ethylbenzene
4. m,p-xylene
5. o-xylene
6. Isopropylbenzene
7. n-Propylbenzene
8. 1-methyl-3-ethylbenzene, 1-methyl-4-ethylbenzene
9. 1,3,5-trimethylbenzene
10. 1-methyl-2-ethylbenzene
11. 1,2,4-trimethylbenzene
12. sec-butylbenzene, n-butylbenzene
13. Unknown
14. 1-methyl-3-isopropylbenzene
15. 1,2,3-trimethylbenzene
16. 1-methyl-2-isopropylbenzene
17. 1-methyl-3-n-propylbenzene, 1,3-diethylbenzene
18. 1-methyl-4-n-propylbenzene, n-butylbenzene, 1,4-diethylbenzene, 1,2-dimethyl-5-ethylbenzene
19. 1,2-dimethylbenzene
20. 1-methyl-2-n-propylbenzene
21. 1,4-dimethyl-2-ethylbenzene
22. 1,3-dimethyl-4-ethylbenzene
23. 1,2-dimethyl-4-ethylbenzene
24. 1,3-dimethyl-2-ethylbenzene
25. Unknown
26. 1,2-dimethyl-3-ethylbenzene
27. 1,2,4,5-tetramethylbenzene
28. 1,2,3,5-tetramethylbenzene
29. Unknown
30. Unknown
31. Unknown
32. 1,2,3,4-tetramethylbenzene
33. Unknown
34. Unknown
35. Unknown
36. Unknown
37. Naphthalene As noted hereinbefore, computer/controller 600 may be employed to shift data corresponding to various components from one column to another based upon known component elution times for each column.

Figure 8:
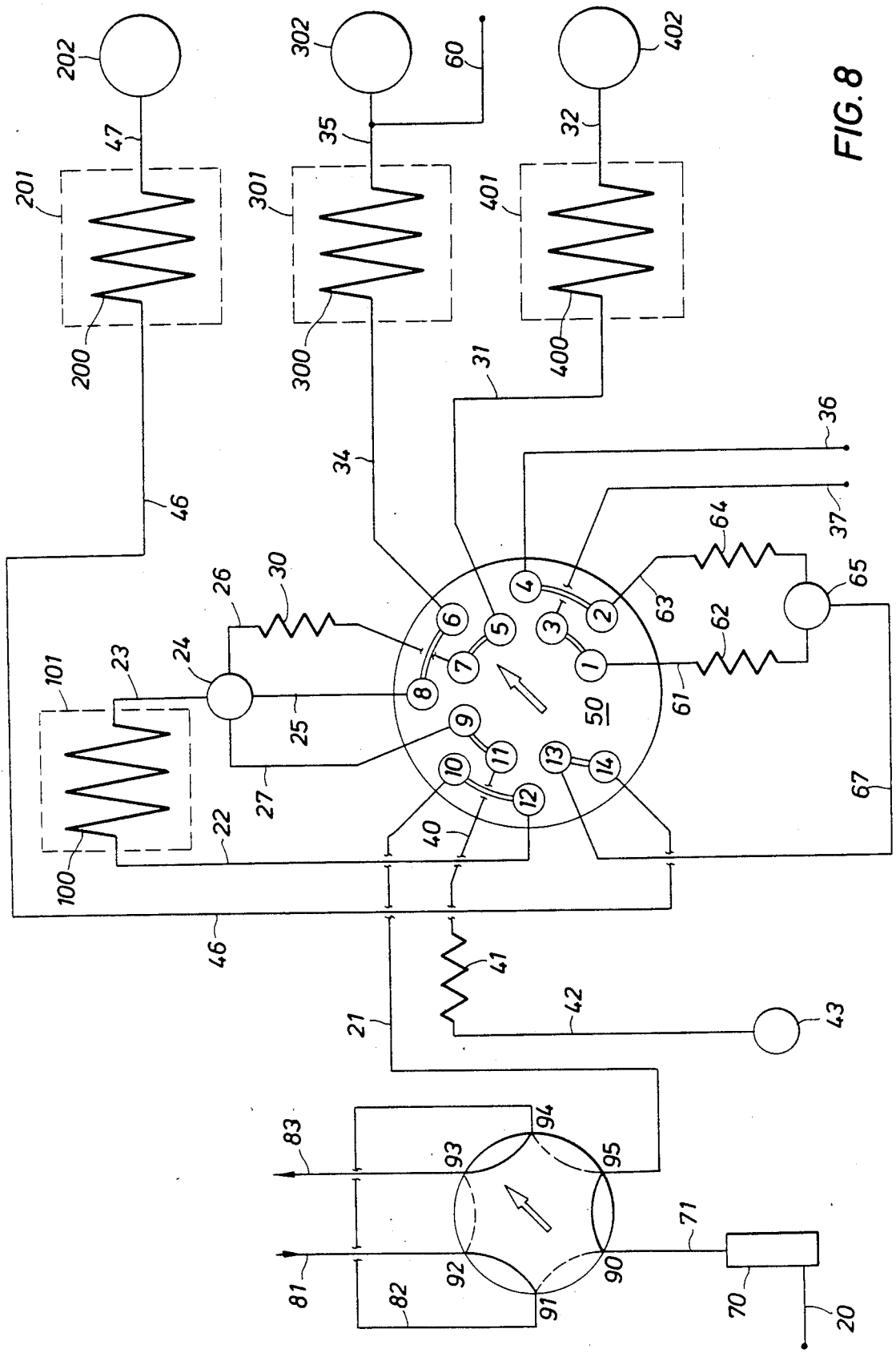
FIG. 8 is an alternative embodiment of the present invention.

Referring to FIG. 8, the sample to be analyzed may again be injected into sample injector 70. The sample is carried from injector 70 by carrier gas from line 71 into line 21. Line 71 is connected to port 90 of valve 60. Valve 60 is a two-position six-port valve. In its first operating position, the ports of valve 60 are interconnected as indicated in FIG. 8 by the solid lines. In its second operating position, the ports of valve 60 are interconnected as indicated by the dashed lines.

The first position of valve 60 may be employed to allow a sample from injector 70 to be supplied to the various columns for analysis. That is, port 90 is interconnected with port 95 to which line 21 is connected. Thus, the sample is swept into line 71 from injector 70 by the carrier gas supplied by line 20. Line 71 is also connected to line 21 through valve 60. Line 21 is the sample supply line for the apparatus of FIG. 1, which operates as described hereinbefore.

As also depicted in FIG. 8, valve 60 may be employed to circulate a portion of a product or feedstock through a sample loop 82 on valve 60 through supply line 81 and return line 83. When this portion of the apparatus depicted in FIG. 8 is so employed, injector 70 need not be used to provide a sample for analysis. When valve 60 is moved to its second position, the carrier gas from line 71 sweeps the sample from sample loop 82 into line 21 where it is directed to column 100 through valve 50, split, and analyzed as noted hereinbefore. Valve 60 may be so employed with the apparatus of FIG. 1.

Many other variations and modifications may be made in the apparatus and techniques hereinbefore described by those having experience in this technology without departing from the concepts of the present invention. For example, other suitable means than the carrier gas flow restrictors 62 and 64 may be used to prevent partial sample transfer to columns 300 and 400. Also, make-up gas on detector 302 (FIG. 1) has been found to improve the detector response, and to improve the response linearity for saturates when nitrogen, carbon dioxide, or argon is mixed in a fixed proportion with the hydrogen carrier gas. Accordingly, it should be clearly understood that the apparatus and methods depicted in the accompanying drawings and referred to in the foregoing description are illustrative only and are not intended as a limitation on the scope of the invention.

What is claimed is:

1. A method for analyzing a hydrocarbon sample containing isoparaffins, normal paraffins, naphthenes and aromatics, comprising:
   separating said aromatics of said sample from said isoparaffins, normal paraffins, and naphthenes of said sample;
   from a first portion of said separated isoparaffins, normal paraffins, and naphthenes, separating isoparaffins, normal paraffins, and naphthenes using pure hydrogen carrier gas and detecting the resulting individual isoparaffins, normal paraffins, and naphthenes having a number of carbon atoms substantially in the range of one to thirteen by carbon number;
   from a second portion of said separated isoparaffins, normal paraffins, and naphthenes, separating and detecting individual isoparaffins, normal paraffins and naphthenes components of said sample for components having a number of carbon atoms substantially in the range of one to nine;
   individually separating and detecting said separating aromatics of said sample.

2. The method as described in claim 1, wherein said step of detecting by carbon number further comprises supplying makeup gas to improve detector response, and to improve the response linearity for paraffins when nitrogen, or carbon dioxide, or argon is mixed in a fixed proportion with the hydrogen carrier gas.

3. A method as described in claim 1, wherein said separating of aromatics from said isoparaffins, normal paraffins, and naphthenes is performed with a gas chromatograph column and said separating being stopped in predetermined relationship to the elution of benzene from said column.

4. Apparatus for analyzing a hydrocarbon sample comprising:
   a 13X molecular sieve coated capillary column constructed so as to separate isoparaffins, normal paraffins, and naphthenes by carbon number;
   a first polar column constructed so as to individually separate paraffins and naphthenes;
   a second polar column constructed so as to separate individual aromatics; and
   a highly polar column constructed so as to separate aromatics from non-aromatic components, each of said polar columns being connected by flow conduit means to a valve means constructed so as to simultaneously supply said non-aromatic components to said 13X molecular sieve column and first polar column, said valve means in addition simultaneously supplying said aromatic components to said second polar column, said first and second polar columns being less polar than said highly polar column.

5. The apparatus described in claim 4, further comprising means for controlling the temperature of said 13X molecular sieve column.

6. The apparatus of claim 5, further comprising means for controlling the temperature of said first polar column.

7. The apparatus described in claim 4, wherein said valve means is constructed so as to selectively interconnect said highly polar columns with said second polar column.

8. The apparatus described in claim 4, further comprising computer/controller means for operating said 13X molecular sieve column, said first polar column, said second polar column and said highly polar column.

9. The apparatus described in claim 4, further comprising flow restrictor means operably connectable to at least one of said columns to maintain predetermined gas pressures for assuring complete sample transfer to said column.

10. The apparatus described in claim 4, further comprising hydrogen carrier gas means for supplying hydrogen for separating the isoparaffins, normal paraffins, and naphthenes in said columns.

* * * * *